United States Patent [19]

Perry, Jr.

[11] Patent Number: 4,934,378
[45] Date of Patent: Jun. 19, 1990

[54] BRUXISM METHOD AND APPARATUS USING ELECTRICAL SIGNALS

[76] Inventor: John D. Perry, Jr., 242 Old Eagle School Rd., Strafford, Pa. 19087

[21] Appl. No.: 331,223

[22] Filed: Mar. 31, 1989

[51] Int. Cl.$^5$ .............................................. A61B 5/10
[52] U.S. Cl. .................................... 128/733; 128/777; 128/905
[58] Field of Search ................ 128/733, 774, 776–777, 128/782, 642, 630, 903, 905

[56] References Cited

U.S. PATENT DOCUMENTS

| | | | |
|---|---|---|---|
| 3,368,551 | 2/1968 | Hardyck | 128/733 |
| 3,996,666 | 12/1976 | Blanque | 128/777 X |
| 4,267,838 | 5/1981 | McCall | 128/789 X |
| 4,355,645 | 10/1982 | Mitani et al. | 128/777 |
| 4,396,019 | 8/1983 | Perry, Jr. | 128/733 |
| 4,556,063 | 12/1985 | Thompson et al. | 128/903 X |
| 4,669,477 | 6/1987 | Ober | 128/782 X |
| 4,715,367 | 12/1987 | Crossley | 128/733 X |

FOREIGN PATENT DOCUMENTS 3635188 4/1988 Fed. Rep. of Germany ...... 128/733

*Primary Examiner*—Angela D. Sykes
*Attorney, Agent, or Firm*—Eliot S. Gerber

[57] ABSTRACT

The invention measures the electrical signals at the microvolt level emitted from the masseteric (jaw) muscle when bruxism occurs. The apparatus detects electrical signal impulses from electrodes on a transducer probe located within one of the patient's ear channels and transmits the detected signals to an amplifier. in one embodiment, a circuit converts the signal information into an audible tone. The tone provides the immediate knowledge of the bruxism which leads to controlling of the action. The apparatus may be worn inconspicuously during the day and without discomfort while asleep for sleep interruption feedback.

15 Claims, 3 Drawing Sheets

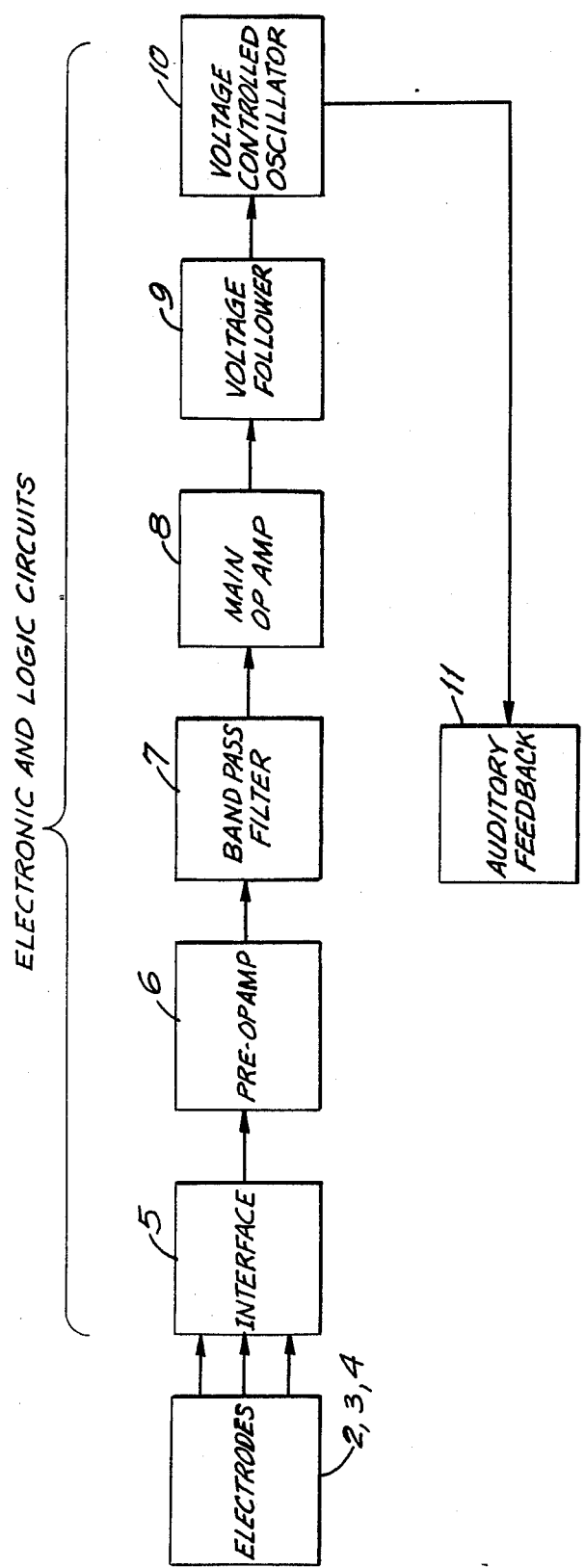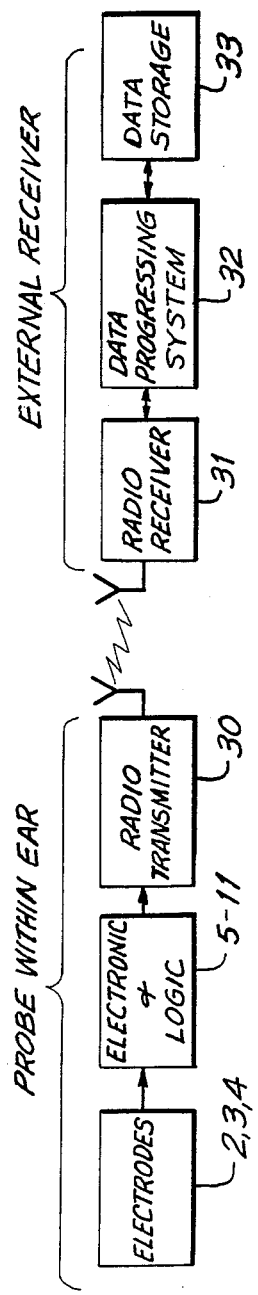
FIG.7
FIG.8

BRUXISM METHOD AND APPARATUS USING ELECTRICAL SIGNALS

BACKGROUND OF THE INVENTION

1. Field of the invention

The present invention relates to the dental methods and apparatus for the treatment of bruxism, i.e., the grinding of teeth. Bruxism is the abnormal excessive and non-functional nocturnal or subconscious grinding of teeth. Clinically significant bruxism may ruin the teeth and may indicate, or lead to, temporomandibular Joint Dysfunction (TMJ) or Myofascical Pain Dysfunction (MPD).

2. Description of the Prior Art

In TMJ the muscles used for chewing and the joints of the jaw fail to work in conjunction. Due to emotional stress, some people clench their teeth so hard that they jolt their jaw out of its natural position, resulting in TMJ. The misalignment of the temporomandibular joint (jaw joint) causes muscle spasms, resulting in pain in front of the ear and in the head. Thee pain may also spread to the neck, shoulders and back.

The initials MPD have been used to refer to similar terms: "myofascial", "myofacial", "masticatory" or "mandibular" pain dysfunction, see Schwartz, M. Biofeedback: A Practitioner's Guide, Ch 16, pgs. 288-307 (1987).

Typical symptoms of TMJ include cracking or popping sounds from the joint, chronic headaches, and limited movement of the jaw. There presently exist quite a few forms of treatment of bruxism and TMJ. A popular remedy is the insertion of a bit plate made of acrylic. It is worn either at night or 24 hours a day, from three to six months. When worn during the day, it may be unsightly. Other forms of relief, especially from TMJ, are hot and cold compresses, aspirin, muscle relaxants, facial exercise, equilibration (dentist grinds certain teeth to repair the bite), injection of salt solutions or procaine to break up the sensitive points the muscle, surgery to reconstruct the temporomandibular joint (a small percent choose this), massage—to increase the blood circulation and relax the muscle, and biofeedback and relaxation therapies.

An article in the *Journal of Consulting and Clinical Psychology*, 52: 928-935, 1984, discusses "Biofeedback and Relaxation". In this biofeedback therapy article, silver-silver chloride electrodes were taped bilaterally over the masseteric area (external jaw area). Upon biting down, the digital multimeter increased or the frequency of an audible tone increased. When the patients realize they are grinding their teeth, they stop. The patients were also given general relaxation instructions to follow for 20 minutes each day. Although this biofeedback technique accurately senses the teeth grinding, it is a large device and not portable, so that it cannot be used during the day. The electrodes for example, are three electrodes on the surface of the cheek. Such electrodes are objectionable as they are disfiguring and reveal the patient's problem to others. Consequently, such cheek electrodes are not often used during the day, when they would be most useful. Schwartz, supra, at 292, discusses the use of strip chart recorders for recording facial muscle activity.

The acrylic bite plate is widely accepted in dental practices as a treatment for bruxism. Some patients who have used it appear cured two years later; however, others continue to suffer.

U.S. Pat. No. 4,355,645 shows a device utilizing an electromyographic amplifier and electrodes attached to the patient's masseter and temporal regions to display the EMG potential of the masticatory muscles.

U.S. Pat. No. 3,813,671 shows a flexible mouthpiece used as a multilayer bruxism monitoring device.

U.S. Pat. No. 3,696,666 senses auscultation of the motion and position of the patient's mandible using an external displacement pickup.

U.S. Pat. No. 4,396,019 to the same inventor as herein, incorporated by reference herein, shows a vaginal myograph apparatus using a probe to detect electrical signals from the pubococcygeus muscle of the patient.

SUMMARY OF THE INVENTION

This invention measures the electrical signals at the microvolt level emitted from the masseteric muscle (the jaw muscles) when bruxism occurs. The apparatus detects electrical signals impulses from electrodes on a transducer probe located within one of the patient's ear channels and transmits the detected signals to an amplifier, preferably in the device. In one embodiment, a circuit converts the signal information into an audible tone. The tone provides the immediate knowledge of the bruxism which leads to the controlling of the action. This is a form of electromyographic ("EMG") feedback and that general technique has been successfully used in other situations to treat stress-related illnesses. The apparatus may be worn inconspicuously during the day and without discomfort while asleep for sleep interruption biofeedback.

OBJECTIVES AND FEATURES OF THE INVENTION

An objective of this invention is to create an electromyograph ear-insert which detects the emittance of electricity in the jaw muscle to help in the cure of bruxism.

It is another objective to provide a device which is small and inconspicuous and portable so that it can be worn the entire day and so comfortable that it may be worn all night long.

It is another objective of the present invention to provide such an electromyographic feedback device (EMG) that will remind the patient of his unconscious masseter muscle activity by providing him a biofeedback signal when such activity occurs, such biofeedback teaching the patient to relax his masseter muscle without further intervention.

It is another objective of the present invention to provide such an electromyographic feedback device EMG) that will fit into the ear channel and so it will be socially inconspicuous or appear to be a hearing aid.

It is another objective of the present invention to provide such an electromyographic feedback device (EMG) that does not require adhesion to the cheek and does not require external support to stay in place in the ear channel.

It is another objective of the present invention to provide such an electromyographic feedback device (EMG) that may rapidly and conveniently be turned off, or removed from the ear, when the patient is eating and is thereafter easily turned on or reinserted into the ear channel.

It is another objective of the present invention to provide such an electromyographic feedback device (EMG) that may easily be removed to replace its batteries.

It is a feature of the present invention to provide a method and apparatus in dental bruxism for the detection and biofeedback of the daytime subconscious, and sleeping, teeth grinding of a patient.

A small elongated probe is inserted into the ear channel of the patient. The probe has an insulative base and a plurality of electrodes mounted on its exterior in contact with the wall of the ear channel. The electrodes detect microvolt level electrical signals at the wall of the ear channel arising from movement of the muscles of the temporomandibular joint during teeth grinding. Those signals are amplified, by amplifier means, and filter means electronically distinguish the signals from ongoing electrical activity. The distinguished signals are used to operate warning means, such as a tiny audio speaker, to warn the patient by a tone or voice command that he is grinding his teeth. In one embodiment, preferably the entire device fits within the ear of the patient.

BRIEF DESCRIPTION OF THE DRAWINGS

The supplied figures illustrate this invention, where:

FIG. 7 shows, in block diagram form, the electronic circuitry of the present invention; and FIG. 8 shows an embodiment using a radio transmitter and receiver.

DETAILED DESCRIPTION OF THE INVENTION

Figure 1A:
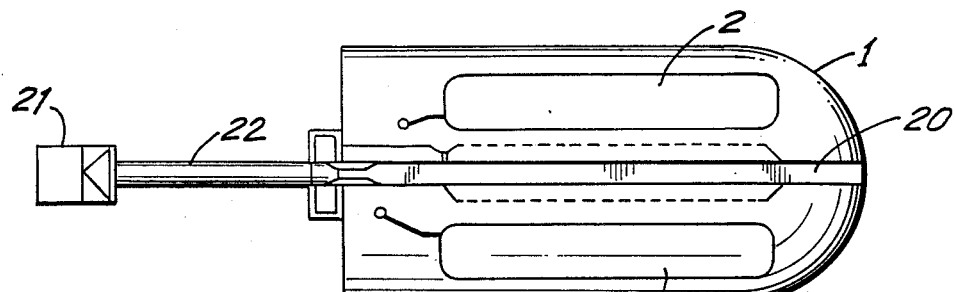
FIG. 1A is a side plan view showing the probe part of the ear electromyograph illustrating the three electrodes.

FIG. 1 shows the preferred embodiment of the EMG probe of the present invention, in which the electronics are within the probe body 1. In general, the probe body 1 consists of a very small cylinder probe body of about 0.3 cm to 0.7 cm wide and 0.5 to 1.0 cm long, preferably 0.04 cm wide and 0.5 cm long. The probe body is of an inert plastic resin which is an electrically non-conductive material. Body 1 supports two active conductive electrodes 2,3 and a neutral or ground conductive electrode 4. The electrodes are preferably a noble metal, preferably silver, but alternatively may be of a conductive plastic. The electrodes 2, 3 and 4 detect electrical signals coming from the jaw muscle.

The cylinder body 1 is formed from a sealing plastic resin material, for example, pourable acrylic resin, to make it watertight, sterilizable and mechanically strong. The body has an air passage 20 so the user may hear conversations and otherwise hear normally. The audio speaker 21 fits behind the ear and is connected by air tube 22 to a piezoelectric tone generator within the probe body 1.

Figure 1B:
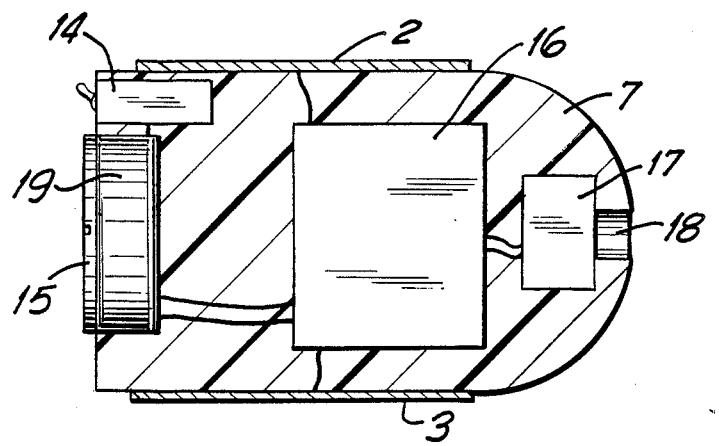
FIG. 1B is a side cross-sectional view of the probe of FIG. 1.
Figure 2:
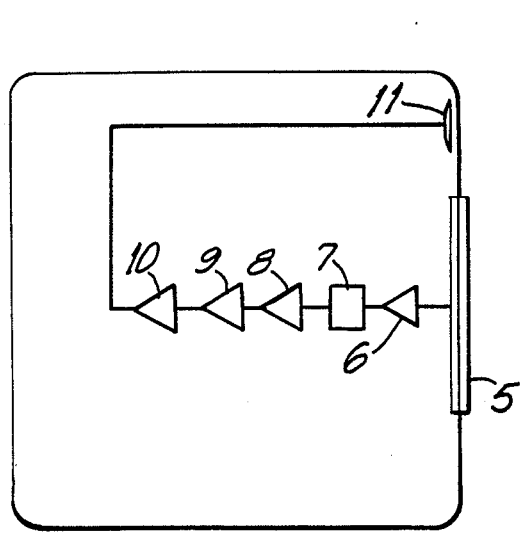
FIG. 2 is a side cross-sectional view showing, in block form, the electronic and logic circuits for amplifying and transforming the input signals into useful biofeedback sounds.

The electronic circuits to detect and process the signal detected at the wall of the ear channel are shown in FIG. 2. The connection between the electrodes 2-4 and the electronic circuits, shown in FIG. 2, is made at the interface 5. The electrodes 2, 3 and 4 are electrically connected to interface 5. Electronic signals emitted from the jaw muscle are detected by electrodes 2, 3 and transmitted through the interface 5 to the differential inputs of an operational amplifier pre-amplifier 6 which includes a FET (field effect transistor) input stage or alternatively extremely sensitive transistor. In the embodiment of FIG. 1 the interface is within the probe body 1. The detected signals pass thorugh a 100-600 Hz bandpass filter 7 and the signals then pass through the main amplifier 8. The signal is then buffered by a unity-gain voltage follower 9. A voltage controlled oscillator 10 drives an audio transducer output device 11, which may be speaker producing a low volume pitch because it is located right next to the eardrum. A piezoelectric tone generator only 0.2 cm ×0.2 cm is sufficient. The external shape and size of the body cylinder, shown in FIG. 2, will be determined by each individual's ear size and is preferably fitted to suit each individual. The probe of FIG. 1B includes on-off switch 14, battery cover 15, the encapsulated electronic circuits 16 (shown in FIG. 7), audio speaker 17, air hole 18 and battery 19.

The range of the electrical signals arising from jaw muscle activity during teeth grinding which is detectable at the wall of the ear channel is in the range of 1-25 microvolts RMS (root mean square) and 100-600 Hz. The band pass filter is set at 100-600 Hz to reduce interference from common household sources. The amplification is in the range of 0.5 to 2 million so that the output to the tone generator is in the 1-2 volt range.

Figure 3:
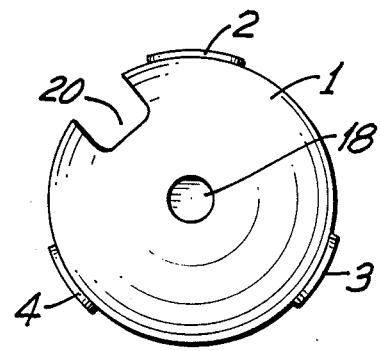
FIG. 3 shows a frontal plan view of the cylindrical probe of FIG. 1.

FIG. 3 shows the cylindrical probe from the front.

Figure 4:
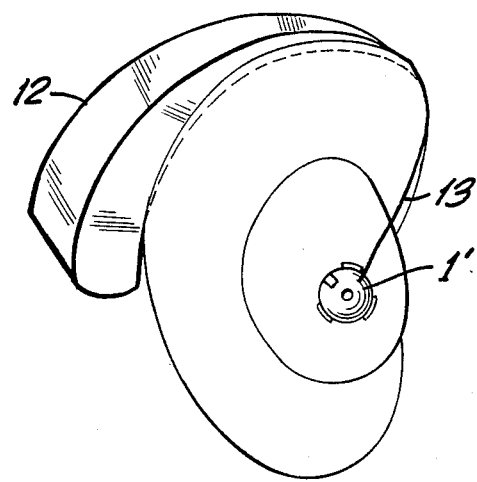
FIG. 4 shows a side view of an ear with the device fitting behind the ear and a wire connecting it to a probe inserted in the ear.

The embodiment of the device shown in FIG. 4 has the same internal components as the embodiment of FIG. 2, but the circuitry and its case 12 are structured to fit above the ear. The case 12 rests above the ear 12, and a wire 13 connects case 12 to the probe 1' at the ear channel of the ear. In this embodiment interface 5 is at the probe 1' and the electronics is within the case 12.

Figure 5:
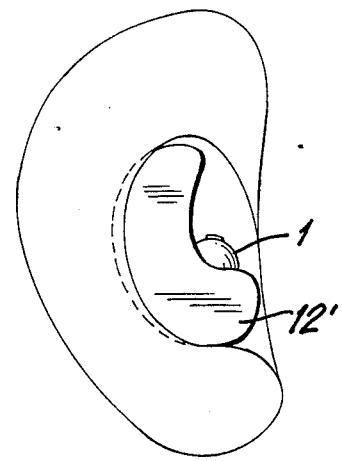
FIG. 5 shows a side view of the ear with the device sitting in the inner ear lobe.
Figure 6:
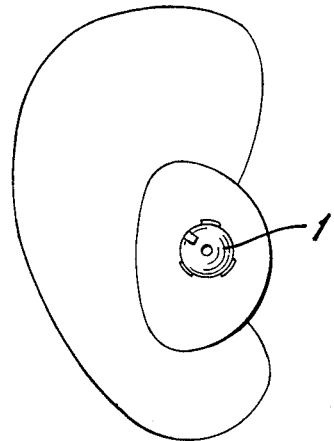
FIG. 6 shows a side view of the ear with a miniature device fitting entirely within the ear canal.

In the embodiment of FIG. 1, the speaker 21 is the only portion worn behind the external ear. The case 12' in the embodiment of FIG 5 has the same internal components as the case 12 of FIG. 4, but its case 12' is structured to fit inside the inner ear lobe. The probe of FIG. 1 is joined directly to the circuitry of FIG. 2 (within the case) which fits within the external ear. In the embodiment of FIG. 6 the entire device is made sufficiently small so that it fits in the ear canal, including the audio speaker.

In all embodiments, the device is battery operated. A disadvantage of the embodiment shown in FIG. 4 is that it is more noticeable and the buzzer might have to be louder due to the greater distance from the eardrum. If worn during the day, others might hear it.

When the patient hears the warning buzzer, he will cease grinding his teeth. The device is removed, or switched off, during periods of eating or conversation. Alternatively, the device may continue to operate but the tone will be generated only once during a period, for example, once each 10-minute period.

In an alternative embodiment, not shown in the drawing, the warning buzzer is replaced by a spoken message, for example, informing the patient that "you are grinding your teeth". That message is generated preferably by a solid-state computer chip within the earpiece.

Another embodiment uses a microcomputer, within the earpiece, which (i) detects background (ongoing) EMG level, i.e., the ambient electrical noise detected by the probe from the wall of the ear channel and (ii) establishes new threshold levels, for example, daily, by processing the detected background EMG over a predetermined period. For example, the mean level of the background level is determined over a 10-minute period, and the threshold is set at 200% of the mean. This will set-off the warning audio signal if the detected electrical signal exceeds the mean (threshold) by 200%, which would occur with teeth grinding.

A still further embodiment, shown in FIG. 8, has a tiny radio transmitter 30 which is within the earpiece, i.e., within the body of probe body 1. The transmitter, preferably a room range FM transmitter, broadcasts to the receiver 31, which may be on the bedside, table, etc. Thee receiver 31 is part of a data processing system 32 which includes data storage 33. The patient's EMG data, from the ear channel, is received and stored over a period, for example, 1 to 2 hours, in order to obtain baseline data. The data storage 33 may be computer memory, such as a floppy or hard disk, or a strip chart in a strip chart recorder.

The data processing system 32, in an embodiment, generates responsive information in response to the patient's teeth grinding activity. It may, using a synthesized voice, tell the patient that he is grinding his teeth, the number of times he has ground his teeth during the last hour, or transmit complex autogenic or self-hypnotic relaxation instructions, either loud enough to be heard or softly for subliminal sleep training.

A number of distinct embodiments of the device are herein disclosed.

First: An ear-plug device fits snugly within the ear canal and is connected to wires to carry electrical signals to an external EMG amplifying and/or feedback device. The external EMG device may be a conventional EMG feedback device. The external EMG device may fit in a shirt pocket.

Second: A combination of an audio device (e.g., air tube, or earphone and air tube) and the probe. Wires connect the electrodes to an external amplifier. Wires also connect the external EMG device to the internal earphone. The external EMG device may be a "shirt-pocket" instrument, or a much larger table/desk mounted device.

Third; Behind-the-ear model, as shown in FIG. 4. The probe within the ear channel is connected to the electronics, contained in a case which is placed behind the ear, and connected to the ear-plug probe by an air tube or wires. In one embodiment of the "behind-the-ear" model, the external device contains the audio device and is only an inch or two away from the ear-plug probe and the audio transducer may be contained within the external device, with only an air-tube returning over the ear. The wires from the electrodes are preferably molded into the walls of the air tube.

Fourth: Transmitter and Transmitter-Receiver, shown in FIG. 8. The electronic circuits in this embodiment also include a radio-frequency transmitter in the probe. The probe transmitter broadcasts, within the room, to a sophisticated bedside companion receiver-EMG instrument which performs a data analysis and recording, and possibly also generates audio or other biofeedback signals. The probe-transmitter may be entirely within the ear canal, or partly within the ear canal and partly in the outer ear. The probe transmitter may also include a receiver and audio device, so that the external receiver EMG instrument broadcasts the signals to trigger the audio device to the ear probe.

Fifth: A single probe which combines sensor electrodes, electronic circuitry, including amplifier, band pass filter, audio driver, and audio transducer in a single probe (capsule) which fits entirely within the ear canal. This is similar to "invisible" hearing aid, as shown in FIG. 6. Alternatively, and shown in FIG. 5, the device is within one case in which the probe portion is within the ear canal and the EMG portion is in the external ear. The amplifier, band pass filter, etc. are within the EMG portion.

What is claimed is:

1. A method in dental bruxism for the detection and biofeedback of subconscious and sleeping teeth grinding of a patient, the method comprising the steps of:
   (a) inserting into the ear channel of the patient a socially inconspicuous elongated transducer having an insulative base and a plurality of electrodes exposed on the exterior of the base and in contact with the wall of said ear channel;
   (b) utilizing said electrodes to detect microvolt level electrical signals at the wall of the ear channel, arising from movement of the muscles of the temporomandibular joint during teeth grinding;
   (c) amplifying the said electrical signals using amplifying means;
   (d) electronically distinguishing the said signals from ongoing electrical activity detected by the said electrodes; and
   (e) utilizing the distinguished signals to operate warning means to warn the patient that he is grinding his teeth.

2. A method as in claim 1 wherein said amplifying means and warning means are positioned within said elongated transducer.

3. A method as in claim 1 wherein the electrical signals which are detected are in the range of 1 to 25 microvolts.

4. Apparatus in dental bruxism for the detection and biofeedback of subconscious and sleeping teeth grinding of a patient, the apparatus comprising:
   (a) an elongated transducer probe adapted to be inserted in the ear channel of the patient and having an insulative body and a plurality of conductive electrodes mounted on the surface of said insulative body;
   (b) amplifying means within said probe electrically connected to said electrodes to amplify the microvolt level electrical signals detected by said electrodes at the wall of said ear channel, said microvolt level signals arising from movement of the muscles of the temporomandibular joint during said teeth grinding;
   (c) filter means electrically connected to said amplifying means to distinguish said temporomandibular joint muscle activity from other electrical signals detectable at said ear channel wall and producing verified signals; and
   (d) warning means electrically connected to said filter means to warn when said verified signals occur thereby indicating the grinding of teeth by the patient.

5. Apparatus in dental bruxism as in claim 4 and further including a case which fits in the ear of the patient and wherein said transducer, said amplifying means, said filter means and said warning means are mounted within said case.

6. Apparatus in dental bruxism as in claim 4 wherein the surface of said electrodes adapted to be in contact with the wall of the ear channel are selected from the group of a noble metal and conductive synthetic plastic compounds.

7. Apparatus in dental bruxism as in claim 4 wherein said amplifying means include a plurality of operational amplifiers.

8. Apparatus in dental bruxism as in claim 4 wherein said amplifying means amplifies said signals to the microvolt level range of 1 to 25 RMS microvolts to the level of 1–2 volts.

9. Apparatus in dental bruxism as in claim 4 wherein said filter means includes a band-pass filter in which the pass band is in the range of 100 Hz to 600 Hz.

10. Apparatus in dental bruxism as in claim 4 wherein said warning means is an electromechanical transducer producing an audio signal.

11. Apparatus in dental bruxism as in claim 10 wherein said transducer is a piezoelectric device.

12. Apparatus in dental bruxism as in claim 4 wherein said transducer probe includes a room-area transmitter means to transmit amplified muscle movement signals and a receiver to receive said transmitted signals.

13. Apparatus in dental bruxism as in claim 12 wherein said filter means and said warning means are within said receiver.

14. Apparatus in dental bruxism as in claim 4 wherein said filter means and said warning means are within said probe.

15. Apparatus in dental bruxism as in claim 4 and including a case which fits behind the ear of the patient and wherein said filter means and said warning means are within said case.

* * * * *